(12) United States Patent
Urabe et al.

(10) Patent No.: US 10,002,422 B2
(45) Date of Patent: Jun. 19, 2018

(54) ULTRASOUND IMAGE PROCESSING APPARATUS AND MEDIUM

(71) Applicant: KONICA MINOLTA, INC., Chiyoda-ku, Tokyo (JP)

(72) Inventors: Makiko Urabe, Yokohama (JP); Keisuke Hayata, Takatsuki (JP); Jun Ohmiya, Kyotanabe (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days. days.

(21) Appl. No.: 15/213,623

(22) Filed: Jul. 19, 2016

(65) Prior Publication Data

US 2017/0024883 A1    Jan. 26, 2017

(30) Foreign Application Priority Data

Jul. 21, 2015    (JP) .................. 2015-144139

(51) Int. Cl.
| | | |
|---|---|---|
| *G06K 9/00* | (2006.01) | |
| *G06T 7/00* | (2017.01) | |
| *G06K 9/62* | (2006.01) | |
| *A61B 8/08* | (2006.01) | |
| *A61B 8/14* | (2006.01) | |
| *A61B 8/00* | (2006.01) | |

(52) U.S. Cl.
CPC ............ *G06T 7/0012* (2013.01); *A61B 8/085* (2013.01); *A61B 8/14* (2013.01); *A61B 8/463* (2013.01); *A61B 8/5215* (2013.01); *A61B 8/5223* (2013.01); *G06K 9/6267* (2013.01); *G06K 2209/053* (2013.01); *G06T 2207/10016* (2013.01); *G06T 2207/10132* (2013.01); *G06T 2207/20076* (2013.01); *G06T 2207/20081* (2013.01); *G06T 2207/30096* (2013.01)

(58) Field of Classification Search
CPC ......... A61B 8/14; A61B 8/5215; A61B 8/085; A61B 8/4444; A61B 8/461; A61B 8/463; A61B 8/5223; G06K 9/6267; G06K 2209/053; G06T 2207/10132; G06T 2207/30096; G06T 7/0012; G06T 2207/10016; G06T 2207/20076; G06T 2207/20081; G06T 2207/30204
See application file for complete search history.

(56) References Cited

U.S. PATENT DOCUMENTS

2014/0033126 A1*   1/2014   Kreeger ................ G06F 19/321
                                                         715/821
2015/0087979 A1*   3/2015   Zhang .................. A61B 8/4494
                                                         600/440

FOREIGN PATENT DOCUMENTS

| JP | 2006141997 A | 6/2006 |
| JP | 2014176430 A | 9/2014 |

* cited by examiner

*Primary Examiner* — Tom Y Lu
(74) *Attorney, Agent, or Firm* — Holtz, Holtz & Volek PC (57) ABSTRACT

An ultrasound image processing apparatus includes a structural object extracting unit, an abnormal candidate spot detecting unit and a cine information generating unit. The structural object extracting unit extracts a structural object in an ultrasound image of each frame from ultrasound image data of a plurality of continuous frames. The abnormal candidate spot detecting unit detects an abnormal candidate spot in the extracted structural object. The cine information generating unit generates cine information where the detected abnormal candidate spot is made to be associated with a frame in which the abnormal candidate spot is detected.

13 Claims, 7 Drawing Sheets

ULTRASOUND IMAGE PROCESSING APPARATUS AND MEDIUM

BACKGROUND OF THE INVENTION

1. Field of the Invention

The present invention relates to an ultrasound image processing apparatus and a medium.

2. Description of Related Art

In ultrasound diagnosis, beating of a heart and movement of a fetus can be obtained as ultrasound images with simple operation of applying an ultrasound probe on body surface. Ultrasound diagnostic imaging apparatuses used for performing such ultrasound diagnosis are known. An ultrasound image is obtained by an ultrasound probe sending ultrasound waves inside a subject, the ultrasound probe receiving reflected ultrasound waves and performing various processes to the received signals.

In an ultrasound diagnostic apparatus, real time inside image of a living body can be displayed during examination by continuously displaying one frame of ultrasound image data one after another in chronological order, each frame of ultrasound image data being generated by ultrasound waves being sent and received. Further, video data (cine video data) formed of a plurality of frames of ultrasound image data can be stored, and such data can be replayed after examination.

For example, when making a diagnosis on mammary gland, a reader (a technician or a physician) may replay the cine video data which is obtained by an examiner (a technician or a physician) with an ultrasound diagnostic apparatus to read the images (video) after examination. In such case, the examiner checks the time until an abnormal candidate is shown since the start of examination when registering the data and tells the reader about the time.

As a method to eliminate images unnecessary for making diagnosis and to efficiently search for an images when reading the data after examination, there is known a method provided in an ultrasound diagnostic apparatus where, with respect to replaying a plurality of frames of ultrasound image data, at least one of start and end of ultrasound image data recording is controlled with a predetermined event which is registered in advance being the trigger, the predetermined event is recorded as an attachment information to the ultrasound image data and desired ultrasound image data is searched for on the basis of the attachment information (see JP 2006-141997). The predetermined event is a button operation such as image adjustment operation, change in brightness for a threshold or more between frames when generating a contrast image, etc.

Further, there is known an ultrasound diagnostic apparatus in which ultrasound image data in chronological order is collected, an extraction condition for extracting a predetermined ultrasound image data is stored, ultrasound image data corresponding to the time period when two or more setting items satisfy the extraction condition is extracted (see JP 2014-176430). The extraction condition is an event in connection with an operation, an image quality parameter, collection condition (frame rate, scan range, raw data), a diagnostic condition (Exam Type), etc.

In the case where an examiner orally tells a reader about an abnormal candidate spot, the examiner has to visually recognize the abnormal candidate spot, record a plurality of continuous frames of ultrasound image data so as to include the abnormal candidate spot and remember the time until the abnormal candidate spot is shown since start of image data recording. Thus, a great burden is put on the examiner. In the case where ultrasound image data is searched for in association with exist or non-exist of a predetermined event which is registered in advance or in the case where the extraction condition for extracting a predetermined ultrasound image data is stored and the ultrasound image data corresponding to the time period when the extraction condition is satisfied is extracted, the predetermined event which is registered in advance and the extraction condition may not necessarily match the ultrasound image data in which the abnormal candidate spot exits.

SUMMARY OF THE INVENTION

An object of the present invention is to easily recognize where in the plurality of continuous frames of ultrasound image data is the frame in which an abnormal candidate spot exists.

To achieve the object described above, according to one aspect of the present invention, there is provided an ultrasound image processing apparatus according to one aspect of the present invention, including: a structural object extracting unit which extracts a structural object in an ultrasound image of each frame from ultrasound image data of a plurality of continuous frames; an abnormal candidate spot detecting unit which detects an abnormal candidate spot in the extracted structural object; and a cine information generating unit which generates cine information where the detected abnormal candidate spot is made to be associated with a frame in which the abnormal candidate spot is detected.

Preferably, the ultrasound image processing apparatus further includes: a cine slider generating unit which generates a cine slider which receives an operation to slide and display the plurality of frames of ultrasound image data by arranging a first marker information corresponding to a type of the abnormal candidate spot in the generated cine information at a position of the frame in which the abnormal candidate spot is detected; and a display controller which makes the plurality of frames of ultrasound image data be displayed in a display with the generated cine slider.

Preferably, in the ultrasound image processing apparatus, in a case where a plurality of continuous frames relating to a same type of abnormal candidate spot exist in the plurality of frames of ultrasound image data, the cine slider generating unit generates the cine slider by arranging a second marker information which indicates a region of the plurality of frames relating to the same type of abnormal candidate spot in the generated cine information at a position of the region of the abnormal candidate spot.

Preferably, in the ultrasound image processing apparatus, the cine slider generating unit generates the cine slider by setting one frame for displaying the first marker information corresponding to the type of abnormal candidate spot in the region relating to the same type of abnormal candidate spot and by arranging the first marker information at a position of the set frame.

Preferably, in the ultrasound image processing apparatus, the cine slider generating unit generates the cine slider by setting different colors according to types of abnormal candidate spot to display the first marker information and/or the region relating to the same type of abnormal candidate spot.

Preferably, in the ultrasound image processing apparatus, the cine information generating unit generates the cine information including operating information where a type of operation performed when generating the plurality of frames of ultrasound image data is made to be associated with a frame which is subject to the operation.

Preferably, in the ultrasound image processing apparatus, the cine information generating unit generates the cine information including operating information where a type of operation performed when generating the plurality of frames of ultrasound image data is made to be associated with a frame which is subject to the operation, and the cine slider generating unit generates the cine slider by arranging a third marker information corresponding to the type of operation in the generated cine information at a position of a frame which is subject to the operation.

Preferably, the ultrasound image processing apparatus further includes: a transmitting unit which transmits a driving signal to an ultrasound prove which transmits and receives ultrasound waves to and from a subject; a receiving unit which receives a received signal from the ultrasound probe; and an image generating unit which sequentially generates the plurality of frames of image data from the received signal.

According to a second aspect of the present invention, there is provided a computer readable non-transitory medium which realizes a program to make a computer function as: a structural object extraction unit which extracts a structural object in an ultrasound image of each frame from ultrasound image data of a plurality of continuous frames; an abnormal candidate spot detecting unit which detects an abnormal candidate spot in the extracted structural object; and a cine information generating unit which generates cine information where the detected abnormal candidate spot is made to be associated with a frame in which the abnormal candidate spot is detected.

BRIEF DESCRIPTION OF THE DRAWINGS

The present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

An embodiment and a modification example of the present invention will be described in details with reference to the attached drawings. However, the present invention is not limited to the examples shown in the drawings. In the following description, the same reference numbers are used for the same functions and compositions, and their descriptions are omitted.

Embodiment

Figure 1:
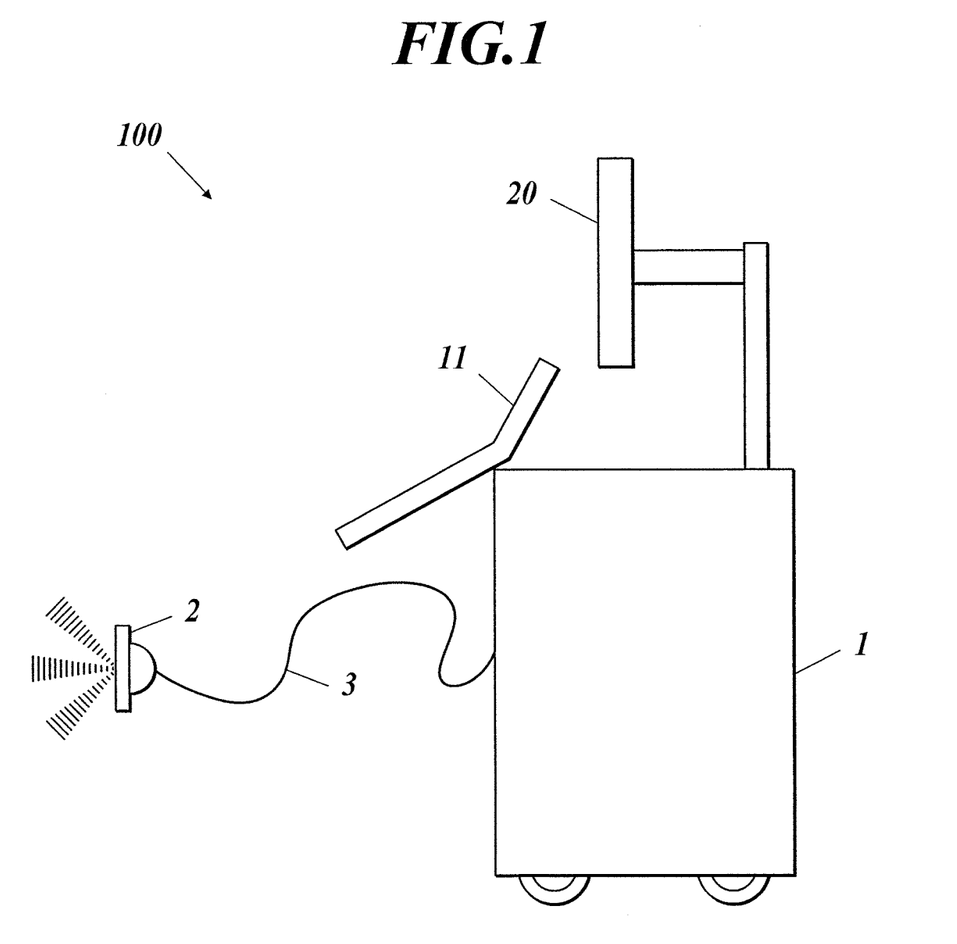
FIG. 1 is an outer image of an ultrasound diagnostic imaging apparatus according to an embodiment of the present invention.

With reference to FIGS. 1 to 8, an embodiment will be described. First, with reference to FIG. 1, the overall configuration of the ultrasound diagnostic imaging apparatus 100 as an ultrasound image processing apparatus of the embodiment will be described. FIG. 1 is an outer image of the ultrasound diagnostic imaging apparatus according to the embodiment.

As shown in FIG. 1, the ultrasound diagnostic imaging apparatus 100 includes an ultrasound diagnostic imaging apparatus main body 1 and an ultrasound probe 2. The ultrasound probe 2 transmits ultrasound waves (transmission ultrasound waves) in to a subject such as a living body (not shown) and at the same time, receives reflected ultrasound waves (reflected ultrasound waves: echo) reflected off inside the subject. The ultrasound diagnostic imaging apparatus main body 1 is connected with the ultrasound probe 2 via a cable 3. The ultrasound diagnostic imaging apparatus main body 1 transmits driving signals which are electrical signals to the ultrasound probe 2 to make the ultrasound probe 2 transmit transmission ultrasound waves to a subject and at the same time, visualizes the internal state of the subject as an ultrasound image on the basis of the received signals which are electrical signals generated in the ultrasound probe 2 in accordance with the reflected ultrasound waves from inside the subject received by the ultrasound probe 2.

The ultrasound probe 2 is provided with transducers 2a (see FIG. 2) which are formed of piezoelectric elements. In the ultrasound probe 2, a plurality of transducers 2a are arranged in the manner of one dimensional array in the orientation direction (scanning direction), for example. In the embodiment, for example, an ultrasound probe 2 provided with 192 transducers 2a is used. Here, the transducers 2a may be arranged in the manner of two dimensional array. Further, the number of the transducers 2a may be set arbitrarily. In the embodiment, a linear electronic scanning probe is used as the ultrasound probe 2 and ultrasound scanning of linear scanning method is performed. However, any scanning method such as a sector scanning method, a convex scanning method, etc. can be applied. Communication between the ultrasound diagnostic imaging apparatus main body 1 and the ultrasound probe 2 can be carried out by wireless communication such as by using UWB (Ultra Wide Band), etc. instead of wired communication via the cable 3.

Figure 2:
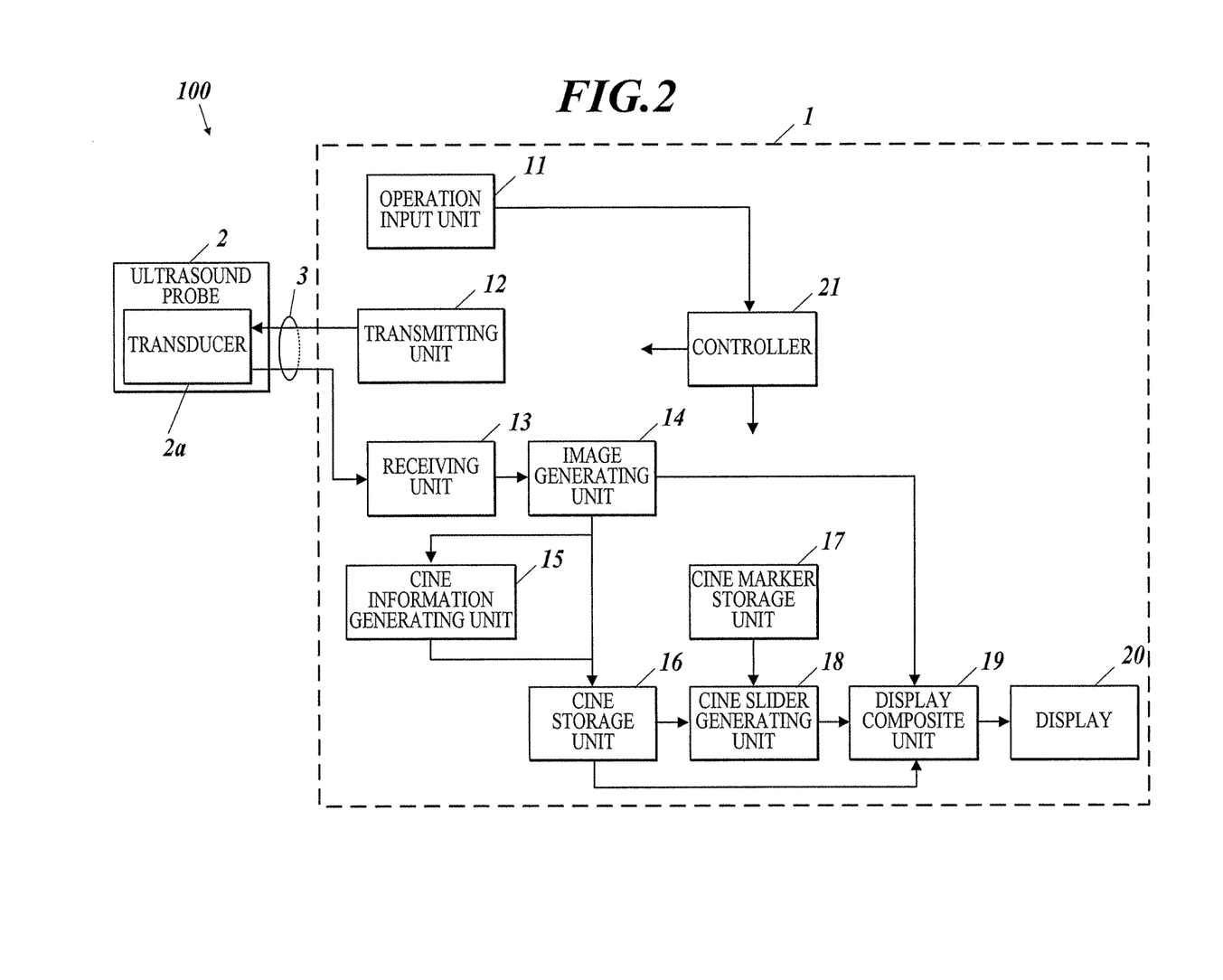
FIG. 2 is a block diagram showing a functional configuration of the ultrasound diagnostic imaging apparatus.

Next, with reference to FIG. 2, a functional configuration of the ultrasound diagnostic imaging apparatus 100 will be described. FIG. 2 is a block diagram showing a functional configuration of the ultrasound diagnostic imaging apparatus 100.

As shown in FIG. 2, the ultrasound diagnostic imaging apparatus main body 1 includes an operation input unit 11, a transmitting unit 12, a receiving unit 13, an image generating unit 14, a cine information generating unit 15 as a structural object extracting unit and an abnormality candidate detecting unit, a cine storage unit 16, a cine marker storage unit 17, a cine slider generating unit 18, a display composite unit 19 as a display controller, a display 20 and a controller 21.

The operation input unit 11, for example, includes various types of switches, buttons, a track ball, a mouse, a keyboard, etc. in order to input a command to instruct staring of diagnosis, data such as personal information of a subject, various types of parameters for displaying an ultrasound image in the display 20, etc. The operation input unit 11 further outputs operation signals to the controller 21. In particular, the operation input unit 11 includes a freeze button which receives an input relating to freezing of an ultrasound image in a video which is being played and input relating to ending of generation of cine video data.

The transmitting unit 12 is a circuit to make the ultrasound probe 2 generate transmission ultrasound waves by supplying a driving signal which is an electrical signal to the ultrasound probe 2 via the cable 3 in accordance with the control of the controller 21. The transmitting unit 12 includes a clock generating circuit, a delay circuit and a pulse generating circuit, for example. The clock generating circuit is a circuit for generating a transmission timing of a driving signal and a clock signal which decides the transmission frequency. The delay circuit is a circuit for setting a delay time for each of the individual paths corresponding to the transducers 2a and for focusing transmission beams (transmission beam forming) which is formed of transmission ultrasound waves by delaying the transmission of driving signals for the set delay times. The pulse generating circuit is a circuit for generating pulse signals as the driving signals at a predetermined cycle. The transmitting unit 12 having the configuration as described above sequentially switches the transducers 2a to which the driving signals are to be supplied by shifting the transducers 2a by a predetermined number of transducers 2a in each transmission and reception of ultrasound waves and carries out scanning by supplying driving signals to the plurality of transducers 2a which are selected to output ultrasound waves in accordance with the control of the controller 21.

The receiving unit 13 is a circuit which receives received signals which are electrical signals via the cable 3 from the ultrasound probe 2 in accordance with the control of the controller 21. The receiving unit 13 includes an amplifier, an A/D converting circuit and a phase addition circuit, for example. The amplifier is a circuit for amplifying the received signals at a pre-set amplifying rate for individual paths corresponding to individual transducers 2a. The A/D conversion circuit is a circuit for performing the analog-digital conversion (A/D conversion) on the amplified received signals. The phase addition circuit is a circuit which adjusts the time phases of the received signals which went through the A/D conversion by providing each path corresponding to each transducer 2a with delay time and generate sound ray data by adding them (phase addition). That is, the phase addition circuit generates sound ray data by carrying out received beam forming with respect to the received signals of individual transducers 2a.

The image generating unit 14 carries out the envelope detector process, logarithmic compression and the like on the sound ray data from the receiving unit 13 and performs brightness conversion by adjusting the dynamic range and gain. Thereby, the image generating unit 14 generates B (brightness) mode image data. That is, B mode image data expresses the strength of received signals in terms of brightness.

The image generating unit 14 includes an image memory unit (not shown in the drawings) which is formed of a semiconductor memory such as a DRAM (Dynamic Random Access Memory). The image generating unit 14 stores the generated B mode image data in the image memory unit in frame units. Image data in frame units may be called ultrasound image data or frame image data.

The image generating unit 14 further performs image processes such as an image filter process, a time smoothing process and the like, as needed, on the ultrasound image data which is read out from the image memory unit as needed and then, the ultrasound image data which went through such image processes is subject to scan conversion into display image pattern so as to be displayed in the display 20. The image generating unit 14 outputs the generated ultrasound image data to the cine information generating unit 15 and the cine storage unit 16 as cine video data, and outputs the ultrasound image data to the display composite unit 19 for real time (live) ultrasound image display.

The cine information generating unit 15 determines whether an abnormal candidate spot such as a lesion exists with respect to each frame of cine video data which is generated in the image generating unit 14. Then, the cine information generating unit 15 generates cine information corresponding to the frame in which an abnormality candidate spot exists among the frames of cine video data and outputs the generated cine information to the cine storage unit 16.

The cine storage unit 16 is formed of a semiconductor memory such as a flash memory, an EEPROM (Electrically Erasable Programmable ROM) or the like, for example. The cine video data which is generated in the image generating unit 14 and the cine information generated in the cine information generating unit 15 are stored in the cine storage unit 16.

The cine marker storage unit 17 is formed of a semiconductor memory such as a flash memory, an EEPROM, a ROM or the like, for example. Marker information for displaying a marker according to the type of abnormal candidate spot such as a lesion and an abnormal candidate region indicating the region of continuous cine frames relating to an abnormal candidate spot in cine video data is stored in the cine marker storage unit 17. Marker information is made to be associated with a cine marker number which identifies the type of cine marker (marker, abnormal candidate spot).

The cine slider generating unit 18 generates a cine slider on the basis of the cine information and the cine video data which are read out from the cine storage unit 16 and the marker information which is read out from the cine marker storage unit 17. Normally, at the time when the cine video data is replayed, the cine slider indicates the replay status such as which frame is currently being replayed. However, the cine slider which is generated in the cine slider generating unit 18 can further indicate in which frame, counting from the first frame, an abnormal candidate spot exists. Furthermore, the cine slider generating unit 18 outputs the cine information which is read out from the cine storage unit 16 to the display composite unit 19.

The display composite unit 19 composites the cine video data which is input from the cine slider generating unit 18 and the cine slider, and outputs the composition of the cine video data and the cine slider to the display 20 as cine screen information.

As for the display 20, any of the display apparatuses such as a LCD (Liquid Crystal Display), a CRT (Cathode-Ray Tube) display, an organic EL (Electronic Luminescence) display, an inorganic EL display, a plasma display and the like can be applied. The display 20 displays cine screens or ultrasound images in the display screen in accordance with image signals of the cine screen information or the ultrasound image data which is output from the display composite unit 19.

The controller 21 includes a CPU (Central Processing Unit), a ROM (Read Only Memory) and a RAM (Random Access Memory), for example. The controller 21 reads out a process program among various types of programs such as the system program and the like stored in the ROM and opens the program in the RAM. In accordance with the opened program, the controller 21 performs centralized controlling of the operation of each component of the ultrasound diagnostic imaging apparatus main body 1. The ROM is formed of a non-volatile memory such as a semiconductor, for example. A system program corresponding to the ultrasound diagnostic imaging apparatus 100, various types of process programs which can be executed on the system program and various types of data such as gamma table and the like are stored in the ROM. These programs are stored in the form of computer readable program codes. The CPU sequentially executes operation in accordance with the program codes. The RAM forms a work area in which various types of programs which are to be executed by the CPU and data according to the programs are temporarily stored. In particular, it is assumed that the first and second cine screen information display programs are stored in the ROM of the controller 21. Here, although the controller 21 controls the individual components of the ultrasound diagnostic imaging apparatus main body 1, lines that express such controlling are omitted in FIG. 2.

With respect to the transmitting unit 12, the receiving unit 13, the image generating unit 14, the cine information generating unit 15, the cine slider generating unit 18, the display composite unit 19 and the controller 21 included in the ultrasound diagnostic imaging apparatus 100, a part of or all of the functions of each function block can be realized as a hardware circuit such as an integrated circuit. Integrated circuit is LSI (Large Scale Integration), for example, and is also called as IC, system LSI, super LSI or ultra LSI according to the level of integration of the LSI. The method to form an integrated circuit is not limited to LSI and can be realized by an exclusive circuit or an all-purpose processor. Alternatively, an FPGA (Field Programmable Gate Array) or a reconfigurable processor can be utilized which can reconfigure the connection and setting of circuits in the LSI. Further, a part of or all of the functions of each function block can be executed by software. In such case, such software is stored in one or a plurality of recording medium such as a ROM, an optical disk, a hard disk and the like. The software is executed by an arithmetic processor.

Figure 3:
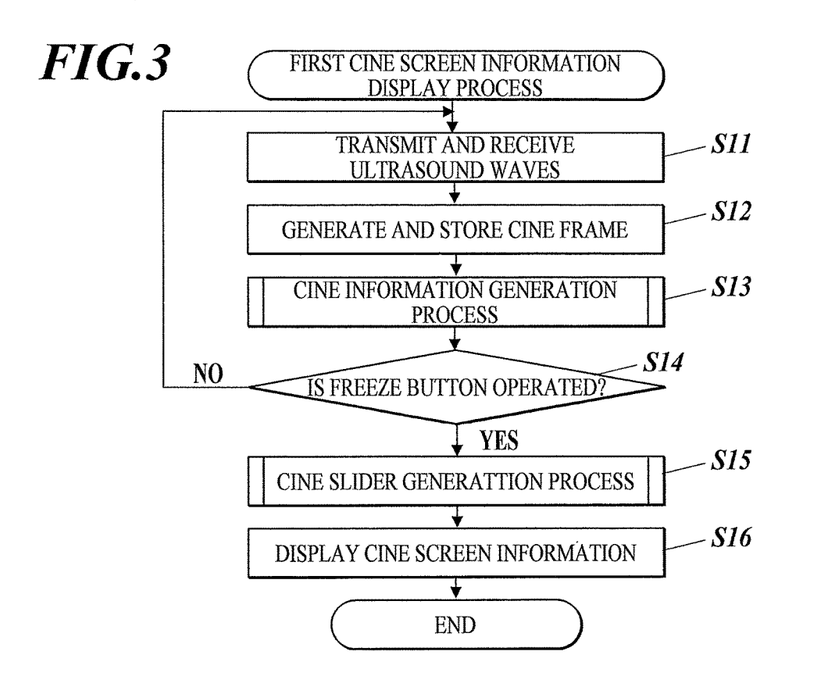
FIG. 3 is a flowchart showing a first cine screen information display process.
Figure 4:
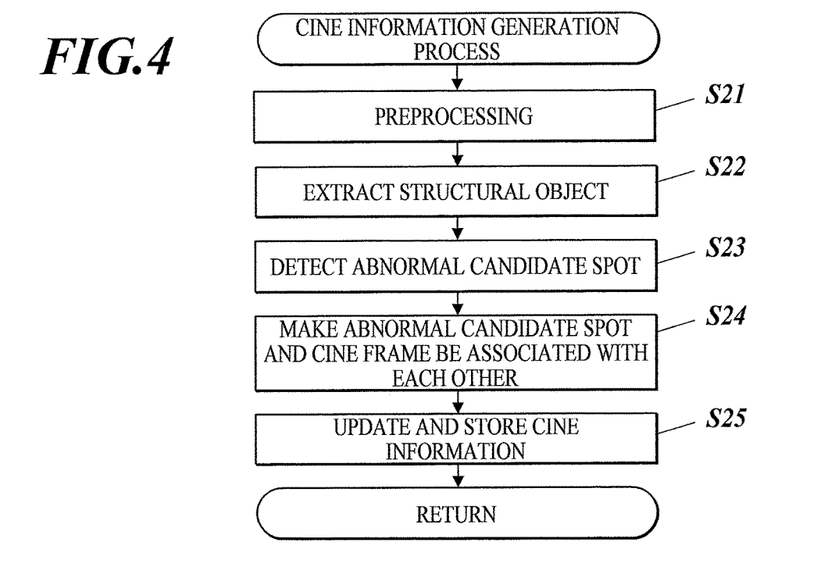
FIG. 4 is a flowchart showing the cine information generation process in the first cine screen information display process.
Figure 5:
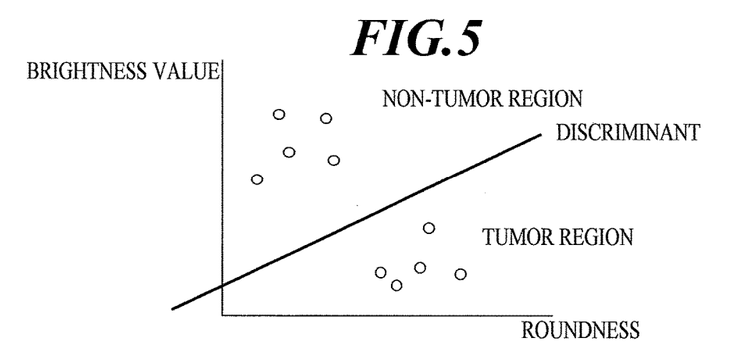
FIG. 5 is a conceptual image used for explaining an example of discriminating method used for tumor discrimination.
Figure 6:
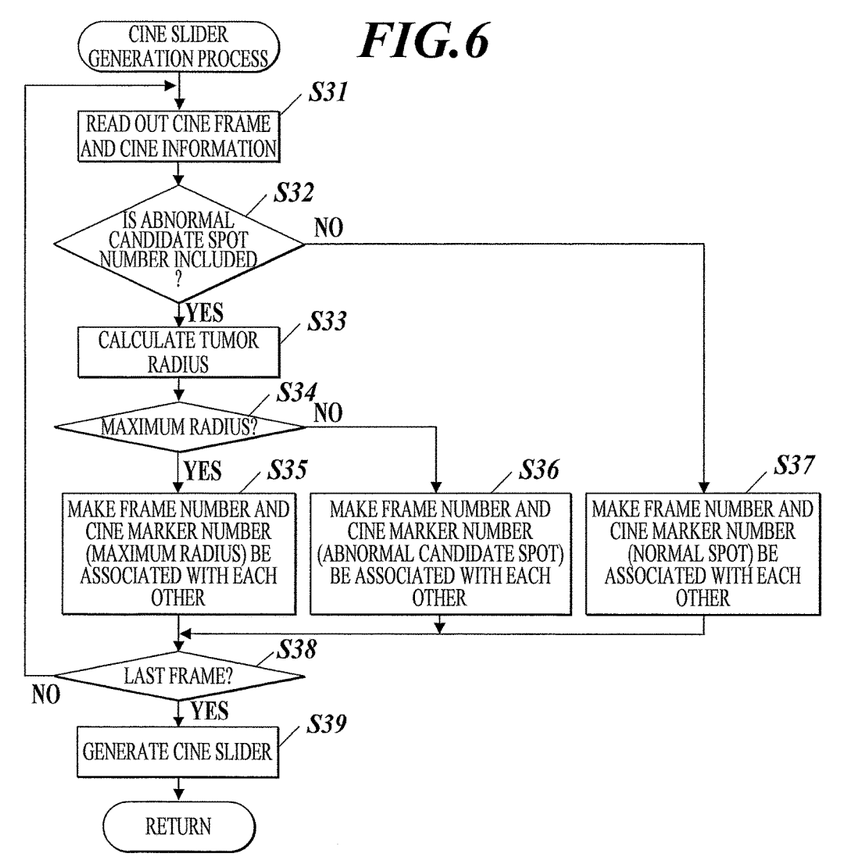
FIG. 6 is a flowchart showing the cine slider generation process in the first cine screen information display process.
Figure 7:
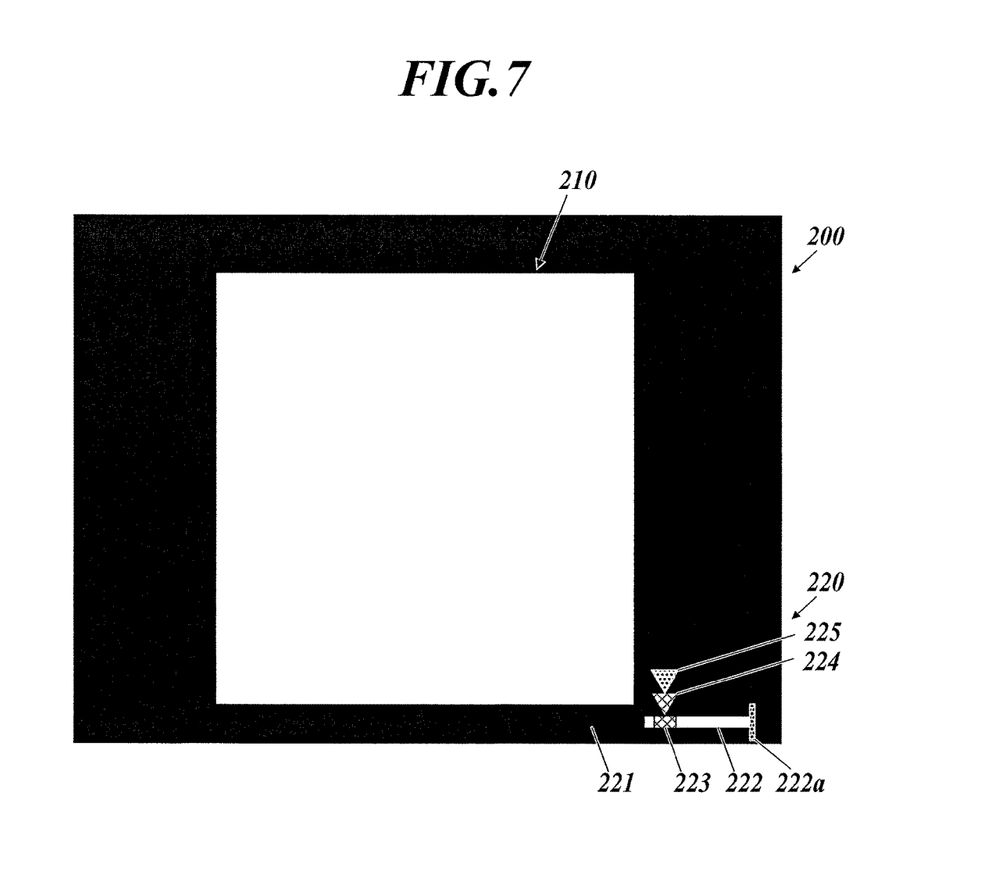
FIG. 7 is a cine screen.
Figure 8:
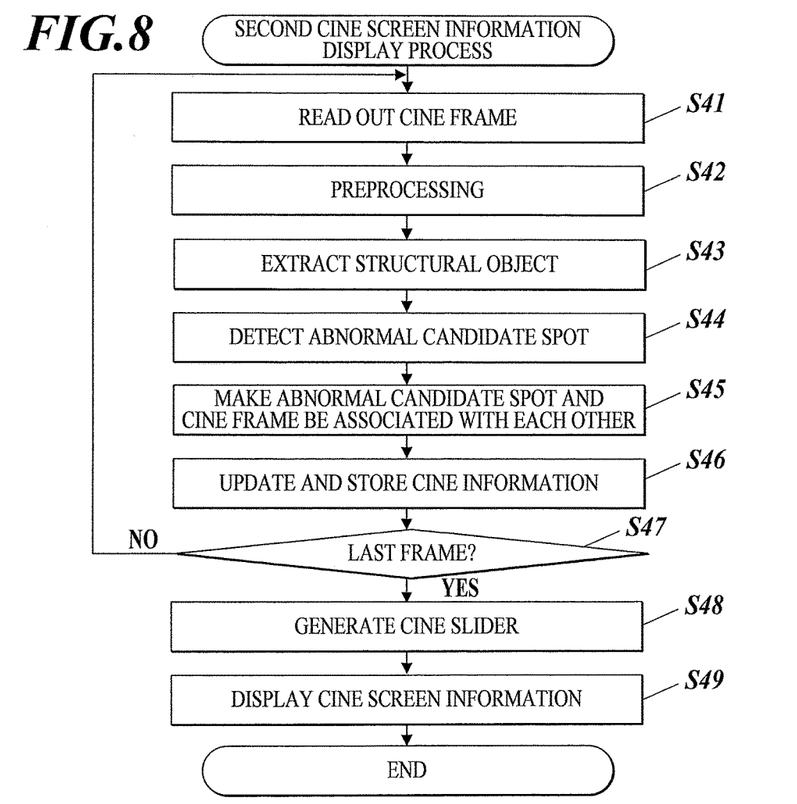
FIG. 8 is a flowchart showing a second cine image information display process.

Next, operation of the ultrasound diagnostic imaging apparatus 100 will be described with reference to FIGS. 3 to 8. In particular, the first and second cine screen information display processes which are executed by the controller 21 will be described. FIG. 3 is a flowchart showing the first cine screen information display process. FIG. 4 is a flowchart showing the cine information generation process in the first cine screen information display process. FIG. 5 is a conceptual image used for explaining an example of discrimination method used to discriminate a tumor. FIG. 6 is a flowchart showing the cine slider generation process in the first cine screen information display process. FIG. 7 is the cine screen 200. FIG. 8 is a flowchart showing the second cine screen information display process.

The first cine screen information display process is a process to generate cine video data which is obtained by transmitting and receiving ultrasound waves, to detect an abnormal candidate spot such as a lesion in a cine frame of the generated cine video data, and to display the cine video data with the cine slider which indicates the cine frame in which the abnormal candidate spot exits.

For example, input of an instruction to execute the first cine screen information display process performed by an examiner (technician or physician) of a subject via the operation input unit 11 being the trigger, the controller 21 controls the individual components in accordance with the first cine screen information display program stored in the ROM to execute the first cine screen information display process.

As shown in FIG. 3, first, the transmitting unit 12 and the receiving unit 13 perform transmitting and receiving of ultrasound waves for one frame of ultrasound image via the ultrasound probe 2 (step S11). Next, the image generating unit 14 generates one cine frame (one frame of ultrasound image data) corresponding to the transmitting and receiving of ultrasound waves in step S11, outputs the generated one cine frame to the cine information generating unit 15, cine storage unit 16 and display composite unit 19, and stores the cine frame as one frame of cine video data in the cine storage unit 16 (step S12). The cine frame which is input in the display composite unit 19 is displayed in the display 20 as real time (live) screen information.

Then, the cine information generating unit 15 executes the cine information generation process (step S13). Here, the cine information generation process of step S13 will be described with reference to FIG. 4. First, the cine information generating unit 15 performs preprocessing such as a dynamic range adjusting, smoothing process and the like on the one cine frame which is generated in step S12 (step S21).

Then, the cine information generating unit 15 performs an arithmetic of a predetermined feature quantity with respect to the cine frame to which the preprocessing is performed in step S21. Thereafter, the cine information generating unit 15 extracts a structural object in the image by a predetermined determination method according to the arithmetic result (step S22).

As for the predetermined feature quantity mentioned in step S22, feature quantity of Hessian analysis, HaarLike feature quantity, LBP (Local Binary Pattern) or the like is used. Hessian analysis is an analysis method by which a cylindrical structure, planar structure, mass structure, noise and the like are estimated by analyzing an eigen value as a feature quantity from the second derivative component information on an XYZ space (=Hessian matrix). In the X-Y scape of an image, as in the embodiment, a linear structure and a mass structure can be estimated ("Multiscale vessel enfancement filtering" Alejandoro F Flangi et al. 1998, MICCAI).

HaarLike feature quantity is a value (regional contrast) where the sum of pixel values in a white region is subtracted from the sum of pixel values in a black region in a rectangle (HaarLike pattern) which is the calculation target in the search window in an image. HaarLike feature quantity is used to determine the detection target (here, a structural object) in the search window by changing the position and size of the HaarLike pattern in the search window and comparing with the contrast in a learning sample.

LBP is an extraction method of a regional feature in an image and a similar image (detection target) can be searched for. Bit output is performed after comparing the value of the target pixel to the values of the surrounding pixels starting from the upper left of the target pixel and going around in the clock-wise direction (the target pixel value or greater: 1, smaller than the target pixel value: 0), and the 8-bit value obtained by arranging the bits in a line is used as the LBP feature quantity.

The predetermined method in step S22 is a threshold treatment, a correlation value judgment, a discriminant analysis, a SVM (Support Vector Machine) or the like. Threshold treatment is a method to determine whether an image is the detection target on the basis of whether the feature quantity of the image is equal to or greater than a predetermined threshold.

Correlation value judgment is a method to determine whether an image is the detection target on the basis of the level of correlation of the feature quantity of the image to the feature quantity of the detection target.

Discriminant analysis is a method to determine whether an image is the detection target by setting feature quantities at a plurality of axis and by judging where the feature quantity which is detected in the analysis target image is found.

SVM is a method to determine whether an image is the detection target by calculating an identification surface which suitably separates the training data of positive and negative examples in a feature space (for example, so as to maximize the margin). Whether an image is the detection target is determined on the basis of in which area the feature quantity of the image is included with the identification surface being the border.

The threshold, discriminant, identification surface or the like in the above described predetermined determination method can be set by Machine Learning. Machine Learning is one of search themes in the area of artificial intelligence, and is a technique that tries to realize the function same as the learning ability that is naturally realized by human in computer. In machine learning, a plurality of sample data is obtained for each category, categories being identified in advance, and a discrimination criterion is prepared on the basis of the sample data. As for the algorithm of machine learning, random forest is known. Random Forest is a model using a group learning in which the decision tree is used as the weak learner (a learner of low accuracy). For example, data which is obtained through performing sampling on teacher data is given to a node and a number of tree structure graphs (decision tree) are prepared to discriminate data by using a number of decision trees.

The cine information generating unit 15 performs a predetermined feature quantity arithmetic with respect to the image of the structural object which is extracted in step S22 and detects an abnormal candidate spot in the structural object by a predetermined determination method according to the arithmetic result (step S23). As for the predetermined feature quantity and determination method in step S23, the feature quantity and determination method described in step S22 are used. In the embodiment an example where the target to be detected as an abnormal candidate spot is a tumor will be described hereinafter. If the abnormal candidate spot is a tumor, the tumor is detected as a mass structural object by Hessian analysis or the like, for example. The roundness of the mass structural object and the average of brightness values of the pixels included in the mass structure are calculated.

FIG. 5 is a conceptual image used for explaining the discrimination method used for tumor discrimination. For example, a case where a graph of two feature quantities in which the vertical axis shows average values of brightness values and the horizontal axis shows the roundness is set and whether a structural object is a tumor as the detection target is determined will be considered. As shown in FIG. 5, teacher data indicating the feature quantities of the structural object which is a tumor and the structural object which is not a tumor is input in the feature quantity graph in advance, and a discriminant which is the border between the tumor region and the non-tumor region is prepared. Then, in step S23, whether the structural object which is extracted in step S22 is a tumor is determined on the basis of in which region the feature quantity of the structural object which is extracted in step S22 is included with the discriminant being the border. If the structural object is a tumor, the abnormal type (tumor) of the abnormal candidate spot is specified.

Then, the cine information generating unit 15 makes the abnormality type of the abnormal candidate spot which is detected in step S23 and the frame number of the cine frame in which the abnormal candidate spot is detected be associated with each other (step S24). Frame number is the identification information of each cine frame in the cine video data and the cine frames are numbered in the order of generation in the image generating unit 14. The cine information generating unit 15 updates the cine information so as to include the frame number (abnormal candidate spot number) of the cine frame in which the abnormal candidate spot is detected which is made to be associated with the abnormality type of the abnormal candidate spot in step S24, stores the updated cine information in the cine storage unit 16 (step S25) and ends the cine information generation process.

Returning to FIG. 3, the cine information generating unit 15 determines whether an examiner operates on the freeze button in the operation input unit 11 (step S14). If the freeze button is not operated (step S14; NO), the process proceeds to step S11.

If the freeze button is operated (step S14; YES), the cine slider generating unit 18 executes the cine slider generation process (step S15). Here, the cine slider generation process in step S15 will be described with reference to FIG. 6. In the cine slider generating unit 18, the cine video data is read out one frame by one frame and a cine marker is given to each frame.

First, the cine slider generating unit 18 reads out the cine frame having the smallest frame number in the cine video data which is not yet read out and the cine information corresponding to this cine frame from the cine storage unit 16 (step S31).

Thereafter, the cine slider generating unit 18 determines whether an abnormal candidate spot number is included in the cine information which is read out in step S31 (step S32). If an abnormal candidate spot number is included (step S32; YES), the cine slider generating unit 18 performs a post processing thereafter according to the abnormal candidate spot number. Here, description is given by assuming that the abnormal candidate spot is a tumor.

The cine slider generating unit 18 calculates the radius of the abnormal candidate spot (tumor radius) in the cine frame which is read out in step S31 (step S33). In step S33, a tumor which is the abnormal candidate spot is detected in similar way as described in steps S21 to S23 of FIG. 4, and the tumor radius is obtained by extracting the contour line of the tumor, for example.

Then, the cine slider generating unit 18 determines whether the tumor radius which is calculated in step S33 is the maximum radius (step S34). In step S34, whether the tumor radius is the maximum is determined in each of the cine frames of the continuous cine frames (abnormal candidate region) including the abnormal candidate spot, the continuous cine frames including the cine frame which is read out in step S31 just before this step. If it is determined that the tumor radius is the maximum radius (step S34; YES), the cine slider generating unit 18 makes the frame number of the cine frame which is read out in step S31 and the cine marker number which indicates that the abnormal candidate spot (tumor) has the maximum radius be associated with each other (step S35). In step S35, the frame number of the cine frame which is read out in step S31 just before this step and the cine marker number indicating that the tumor has the maximum radius are made to be associated with each other and at the same time, the association between the frame number and the cine marker number indicating that the tumor has the maximum radius in the abnormal candidate region including the cine frame which is read out in step S31 just before this step is canceled, and the frame number whose association is canceled and the cine marker number which indicates the abnormal candidate region are made to be associated with each other.

If the tumor does not have the maximum radius (step S34; NO), the cine slider generating unit 18 makes the frame number of the cine frame which is read out in step S31 and the cine marker number which indicates the abnormal candidate (tumor) region be associated with each other (step S36). If there is no abnormal candidate spot number (step S32; NO), the cine slider generating unit 18 makes the frame number of the cine frame which is read out in step S31 and the cine marker number of the normal region be associated with each other (step S37).

After executing steps S35, S36 and S37, the cine slider generating unit 18 determines whether the cine frame which is read out in step S31 just before this step is the last frame of the cine video data (step S38). If it is not the last frame (step S38; NO), the process proceeds to step S31. If it is the last frame (step S38; YES), the cine slider generating unit 18 reads out the marker information of the marker corresponding to the cine marker number which indicates that the tumor has the maximum radius and the marker information of the abnormal candidate region which corresponds to the cine marker number indicating the abnormal candidate region from the cine marker storage unit 17 as needed. Then, the cine slider generating unit 18 generates a cine slider on the basis of the above read out marker information and the association information of steps S35, S36 and S37 (step S39) and ends the cine slider generation process.

After the cine slider generation process, as shown in FIG. 3, the display composite unit 19 performs the cine screen information display (step S16). The display composite unit 19 displays the cine video data which is read out from the cine storage unit 16 and the cine slider which is generated in the cine slider generating unit 18 in the display 20.

Here, an example of cine screen information which is to be displayed in the display unit 20 in step S16 will be described with reference to FIG. 7.

As shown in FIG. 7, the cine screen 200 as cine screen information includes the ultrasound image part 210 and the cine slider part 220. The ultrasound image part 210 is a region where an ultrasound image of a cine frame in the cine video data which is obtained and stored in steps S11 to S14 is displayed. In the ultrasound image part 210 of FIG. 7, the ultrasound image is not shown. The cine slider part 220 is a region where information corresponding to the cine frame which is being displayed in the ultrasound image part 210 and the cine video data thereof is displayed in terms of a cine slider.

The cine slider part 220 includes the image position display part 221, the cine slider 222, the abnormal candidate region 223 and the marker 224. The marker 225 will be described later.

The image position display part 221 is a display element which indicates the position in the display order of the cine frame which is being displayed in the ultrasound image part 210 in the cine video data which is obtained and stored in steps S11 to S14 in terms of number. In FIG. 7, it is indicated that the cine frame of the ultrasound image which is being displayed in the ultrasound image part 210 is the 125th cine frame in the display order (which is the 125th generated) among the total of 125 frames in the cine video data.

The cine slider 222 is a slide bar indicating the position of the cine frame which is being displayed in the ultrasound image part 210. The cine slider 222 indicates the display order of the cine frame which is being displayed in the ultrasound image part 210 among all of the frames in the cine video data which is obtained and stored in steps S11 to S14 by the slider's position on the bar, whether it is on the right or on the left on the bar. The cine slider 222 includes a nob 222a which indicates the position of the cine frame which is being displayed in the ultrasound image part 210 and which can be moved in the left and right directions to be input (operated).

The abnormal candidate region 223 is a cine marker as a display element to indicate the position of the abnormal candidate region on the cine slider 222, the abnormal candidate region being a range over a plurality of continuous cine frames where a tumor is detected as an abnormal candidate spot. In such way, if one abnormal candidate spot exists over the range of a plurality of frames, the abnormal candidate region 223 is displayed on the cine slider 222 so that the range can be visually recognized.

A (upside down triangle) marker is a cine marker as a display element to indicate the position of the cine frame in which the abnormal candidate spot is detected on the cine slider 222. In the embodiment, the marker 224 indicates the position where the maximum radius of the tumor is depicted in the image data in which the tumor is detected as the abnormal candidate spot. Preferably, the display composite unit 19 sets the marker and the abnormal candidate region of the same abnormal candidate spot be in the same color according to the type of the abnormal candidate spot.

The marker 224 is not displayed with respect to all of the cine frames relating to the abnormal candidate region 223 and is displayed with respect to one unique cine frame among all of the cine frames relating to the abnormal candidate region 223. Here, the marker 224 is displayed at the position corresponding to the cine frame in which the tumor has the maximum radius among all of the cine frames relating to the abnormal candidate region 223. That is, the marker 224 and the abnormal candidate region 223 are displayed at the cine frame position having the frame number which is made to be associated with the cine marker number indicating that the tumor has the maximum radius in step S35. Further, the abnormal candidate region 223 is displayed at the cine frame position having the frame number which is made to be associated with the cine marker number indicating the abnormal candidate region in step S36. However, display of the markers is not limited to the display as described above. In the case where the cine frame having the frame number which is made to be associated with the cine marker number indicating that the tumor has the maximum radius is not a continuation of other cine frames relating to the abnormal candidate spot, only the marker may be displayed at the cine frame position having the frame number which is made to be associated with the cine marker number indicating that the tumor has the maximum radius.

Nothing is displayed at the cine frame position having the frame number which is made to be associated with the cine marker number indicating the normal region in step S37. However, this is not limitative in any way. A cine marker as a display element of a region indicating the normal region or the like may be displayed at the cine frame position having the frame number which is made to be associated with the cine marker number indicating the normal region.

Further, a marker may be set at the position corresponding to one cine frame relating to the abnormal candidate region being associated with other feature of the abnormal candidate spot (such as, an abnormal candidate spot is detected and also an examiner has manipulated at the time when the cine frame was generated).

In the cine screen information display in step S16, the cine frames of the cine video data are replayed and displayed in the order from the cine frame having the first frame number to the cine frame having the last frame number with a predetermined time interval therebetween, for example. At this time, the cine frame to be displayed in the ultrasound image part 210 is sequentially switched and the nob 222a of the slider 22 also moves to the right direction accordingly.

Next, the second cine screen information display process will be described with reference to FIG. 8. The second cine screen information display process is a process in which, after cine video data is generated and stored, an abnormal candidate spot such as a leisure is detected in the cine frames of the cine video data, the cine video data is displayed along with the cine slider which indicates the cine frame in which the abnormal candidate spot exists. Here, an example of abnormal candidate spot detection where the leisure is a tumor will also be described.

It is assumed that the process similar to steps S11 and S12 of FIG. 3 is repeatedly executed to generate cine video data and the generated cine video data is stored in the cine storage unit 16 in advance. For example, input of the instruction to execute the second cine screen information display process performed by an examiner of a subject via the operation input unit 11 being the trigger, the controller 21 controls the individual parts in accordance with the second cine screen information display program which is stored in the ROM and executes the second cine screen information display process.

As shown in FIG. 8, first, the cine information generating unit 15 reads out one cine frame whose frame number is the smallest number, which is not yet read out from the cine video data, from the cine storage unit 16 (step S41). Steps S42 to 946 are similar to step S21 to S25 in FIG. 4, and the cine frame which is the target frame from which an abnormal candidate spot is detected is the cine frame which is read out in step S41.

Then, the cine information generating unit 15 determines whether the cine frame which is read out in step S41 just before this step is the last frame of the cine video data (step S47). If the cine frame is not the last frame (step 947; NO), the process proceeds to step S41. If the cine frame is the last frame (step S47; YES), the cine slider generating unit 18 executes step S48 and the display composite unit 19 executes step S49, and thereby, ends the second cine screen information display process. Steps S48 and S49 are similar to the process of steps S15 and S16 in FIG. 3.

In the above described first and second cine screen information display processes, a tumor as an abnormal candidate spot is detected in a cine frame. However, this is not limitative in any way. In the first and second cine screen information display process, other type of abnormal candidate spot such as a calcification, breast duct observation, fatty deposit, other lesion or the like may be detected. Further, two types or more of abnormal candidate spots may also be detected.

For example, in step S23 of FIG. 4, an abnormal candidate spot of a calcification, breast duct observation or a fatty deposit is detected. In steps S24 and S25, the type of abnormal candidate spot (fatty deposit) and the thickness thereof are made to be associated with the frame number of the cine frame in which the abnormal candidate spot is detected to be included in the cine information.

In step S15 of FIG. 3, a cine marker is arranged on the cine slider according to the marker information corresponding to the type of abnormal candidate spot in the cine information such as a calcification, breast duct observation or a fatty deposit. For example, in the case where the type of abnormal candidate spot is a calcification, the cine marker indicating a calcification can be arranged at the position of any one cine frame relating to the abnormal candidate region, which is a calcification, in step S35. In the case where the type of abnormal candidate spot is breast duct observation, the cine marker indicating breast duct observation can be arranged at the position of the first cine frame relating to the abnormal candidate region, which is breast duct observation, in step S35. In the case where the type of abnormal candidate spot is a fatty deposit, the thickness thereof is calculated in step S33 and the cine marker indicating a fatty deposit can be arranged at the position of one cine frame which depicts the fatty deposit having the maximum thickness among the cine frames relating to the abnormal candidate region, which is a fatty deposit, in step S35. The above described arrangement of cine markers are merely examples and is not limitative in any way. For example, the cine marker indicating a tumor may be arranged at the position of the first cine frame, the cine frame at the center or the last cine frame relating to the abnormal candidate region indicating a tumor.

Further, in the first and second cine screen information display processes, a cine marker and an abnormal candidate region may be displayed on the cine slider in correspondence to the operating information which is input by an examiner operating on the operation input unit 11 at the time when the cine frames of cine video data are generated. For example, if an operation input is performed during a loop of steps S11 to S14 of FIG. 3 (generation and storage of one cine frame), the type of operating information relating to the operation input is made to be associated with the frame number of the cine frame which is generated just before to be included in the cine information in steps S24 and S25 of FIG. 4.

Then, in step S15 of FIG. 3, a cine marker is arranged on the cine slider according to the marker information corresponding to the type of operating information in the cine information. For example, in the case where the type of operating information is still image storage, the cine marker indicating the relevant operation is arranged at the position of the corresponding cine frame. For example, the marker 225 relating to the operation (still image storage) is displayed in the cine screen 200 of FIG. 7. The type of operating information is not limited to still image storage, and other types such as printing instruction of the cine frame which is being displayed (not shown in the drawing) to a printer and the like may be applied.

In the second cine screen information display process, generating and storing of cine video data is executed, operating information corresponding to an operation input performed at the time of generating of each frame of the cine video data is obtained and the cine video data and the operating information of individual frames are stored in the cine storage unit 16 in the ultrasound diagnostic imaging apparatus 100 in advance. In steps S45 and S46, cine information is generated according to the operating information of individual frames stored in the cine storage unit 16 and the generated cine information is stored in the cine storage unit 16.

With respect to markers, in the case where a plurality of markers are arranged at the same position on the cine slider 222, they can be arranged vertically with respect to the longitudinal direction (chronological order direction) of the cine slider 222 as in the case of the markers 224 and 225.

Further, an operation region corresponding to a plurality of continuous cine frames may be displayed on the cine slider 222 according to the type of operating information. With respect to the operation region, the position of the marker indicating an operation is set at one position which is the cine frame position of the first frame in the operation region, which is the first in the generation order. However, this is not limitative in any way. The marker indicating an operation may be set at one position such as at the last or at the center in the operation region according to the generation order. Further, it is preferred that the abnormal candidate spot or the marker indicating an operation is arranged at one position in the abnormal candidate region or in the operation region. However, a plurality of abnormal candidate spots or markers indication operations may be arranged.

Moreover, it is preferred that different types of markers are displayed in different colors. For example, in the cine screen 200, the marker 225 corresponding to an operation (still image storage) and the marker 224 corresponding to an abnormal candidate spot which is a tumor are displayed in different colors. According to two types or more of abnormal candidate spots, various types of markers may be displayed in different colors. According to two types or more of operations, various types of markers may be displayed in different colors.

As described above, according to the embodiment, the ultrasound diagnostic imaging apparatus 100 includes the cine information generating unit 15 which extracts a structural object in an ultrasound image of each cine frame from cine video data, detects an abnormal candidate spot in the extracted structural object, and generates cine information where the detected abnormal candidate spot is made to be associated with the cine frame in which the abnormal candidate spot is detected.

Thus, the position of the cine frame in which the detected abnormal candidate spot exists can be displayed by using the generated cine information. Therefore, where in the cine video data is the cine frame in which the abnormal candidate spot exists can easily be visually recognized by a reader. Further, the abnormal candidate spot in the cine video data can be detected automatically and burden on a reader and an examiner can be reduced.

The ultrasound diagnostic imaging apparatus 100 further includes the cine slider generating unit 18 which generates a cine slider by arranging the marker information (marker 224) corresponding to the type of abnormal candidate spot in the generated cine information at the position of the frame in which the abnormal candidate spot is detected and the display composite unit 19 which makes the cine video data display in the display 20 with the generated cine slider. Thus, since the position of the cine frame in which the detected abnormal candidate spot exists can be shown on the cine slider by a marker, where in the cine video data is the cine frame in which the abnormal candidate spot exists can easily be visually recognized by a reader.

Further, in the case where a region of a plurality of continuous frames relating to the same type of abnormal candidate spot exists in the cine video data, the cine slider generating unit 18 generates a cine slider by arranging the marker information (abnormal candidate region 223) which indicates the abnormal candidate region of the abnormal candidate spot at the abnormal candidate region. Thus, the range of a plurality of frames relating to the same type of abnormal candidate spot can easily be visually recognized by a reader.

Further, the cine slider generating unit 18 generates a cine slider by setting the one cine frame where the marker information (marker 224) corresponding to the type of abnormal candidate spot is to be displayed in the abnormal candidate region of the abnormal candidate spot and disposing the marker information at the position of the set cine frame. Thus, since a marker can be displayed on the cine slider at the position corresponding to one cine frame in the abnormal candidate region, visually confused state due to a plurality of cine markers relating to the same type of abnormal candidate spot being displayed can be prevented.

The cine slider generating unit 18 further generates a cine slider where the marker information of the abnormal candidate spot and the abnormal candidate region are set to be displayed in different colors according to the types of abnormal candidate spot. Thus, since cine markers and abnormal candidate regions of different colors can be displayed according to the types of abnormal candidate spot, the difference in the type of abnormal candidate spot can easily be visually recognized by a reader.

Further, the cine information generating unit 15 generates cine information including operating information where the operation type which is carried out during generation of the cine video data is made to be associated with the cine frame which was subject to the operation. Thus, since the position of the cine frame to which the operation was performed at the time of generation can be displayed by using the generated cine information, where in the cine video data is the cine frame to which the operation was performed at the time of generation can easily be visually recognized by a reader. Further, the cine frame which was subject to the operation (to which the operation was performed at the time of generation) in the cine video data can be detected automatically and the burden on a reader and an examiner can be reduced.

Moreover, the cine slider generating unit 18 generates a cine slider by obtaining the marker information (marker 225) corresponding to the operation type indicated in the generated cine information from the cine marker storage unit 17 and by arranging a marker indicating the operation at the position of the cine frame which is subject to the operation. Thus, since the position of the cine frame which is subject to the operation can be displayed on the cine slider by a marker, where in the cine video data is the cine frame which is subject to the operation can easily be visually recognized by a reader.

Modification Example

Figure 9:
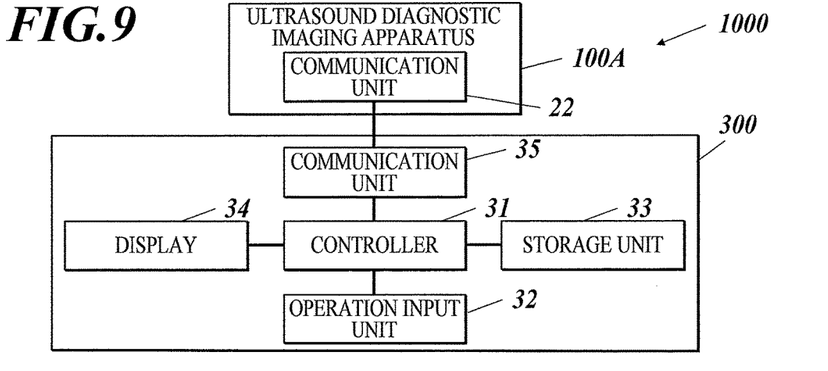
FIG. 9 is a block diagram showing a modification example of an ultrasound diagnostic imaging system.
Figure 10:
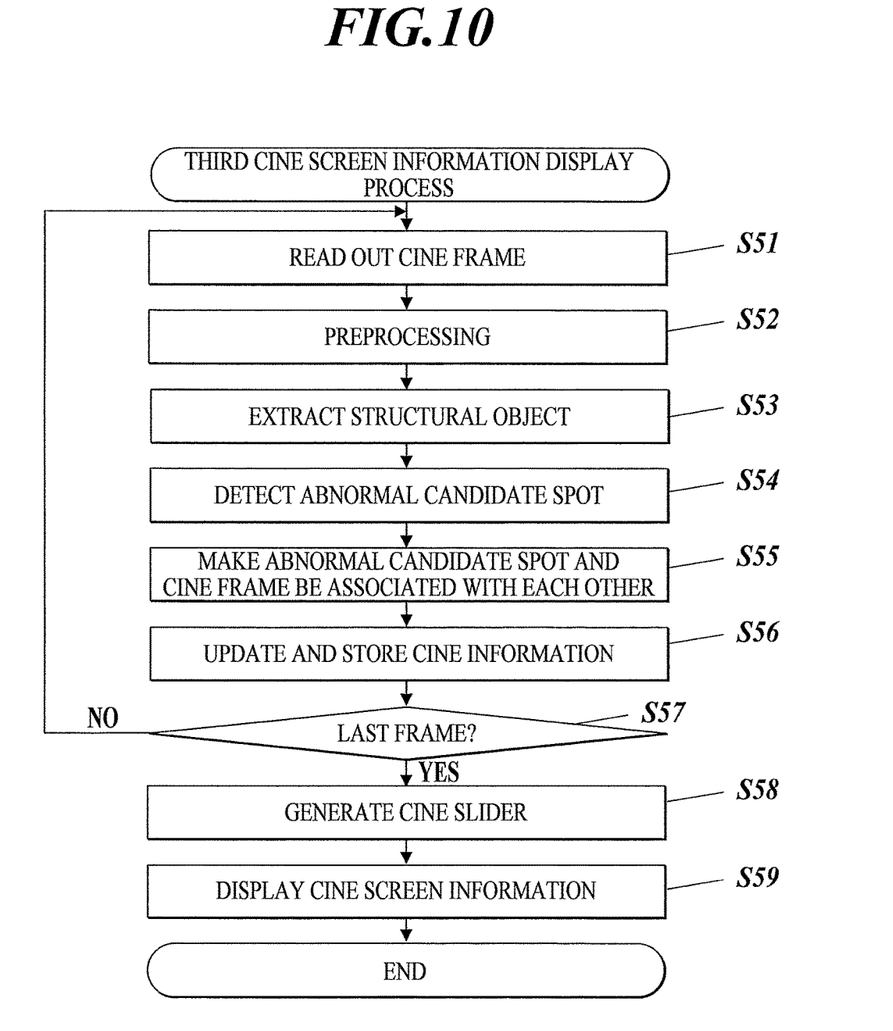
FIG. 10 is a flowchart showing a third cine screen information display process.

A modification example of the above embodiment will be described with reference to FIGS. 9 and 10. FIG. 9 is the block diagram showing the ultrasound diagnostic imaging system 1000. FIG. 10 is the flowchart of the third cine screen information display process.

As shown in FIG. 9, the ultrasound diagnostic imaging system 1000 of the modification example includes an ultrasound diagnostic imaging apparatus 100A and an ultrasound image processing apparatus 300. The ultrasound diagnostic imaging apparatus 100A includes the configuration components that are similar to those of the ultrasound diagnostic imaging apparatus 100 of the embodiment (not shown in the drawing) and further includes a communication unit 22 which is connected to the controller 21.

The communication unit 22 is formed of a communication unit of a wired communication such as via a LAN (Local Area Network) using a cable or a non-wire communication. The communication unit 21 performs communication with the ultrasound image processing apparatus 300.

The ultrasound image processing apparatus 300 includes a controller 31, an operation input unit 32, a storage unit 33, a display 34 and a communication unit 35. The controller 31 includes a CPU and a RAM. The CPU of the controller 31 reads out a program stored in the storage unit 33, opens the program in the RAM and executes the process in cooperation with the opened program. In such way, the CPU of the controller 31 executes various types of processes in cooperation with the programs.

The operation input unit 32 is formed of a keyboard and a pointing device such as a mouse. The operation input unit 32 receives an operation input performed by an operator and outputs the operating information to the controller 31. The storage unit 33 is formed of a HDD (Hard Disk Drive), a SSD (Solid State Drive) or the like, and various types of data and programs are stored in the storage unit 33. It is assumed that the third cine screen information display program and marker information corresponding to the abnormal candidate spot types are stored in the storage unit 33.

The display 34 is a display apparatus such as a CRT display, an organic EL display, an inorganic EL display, a plasma display or the like. The communication unit 35 is formed of a communication unit of the communication method corresponding to the communication unit 22, and performs communication with the ultrasound diagnostic imaging apparatus 100A.

Next, operation of the ultrasound diagnostic imaging system 1000 will be described with reference to FIG. 10. Here, an example where a marker and an abnormal candidate region corresponding to an abnormal candidate spot are displayed will be described.

It is assumed that the process similar to steps S11 and S12 of FIG. 3 is repeatedly executed to generate cine video data and store the generated cine video data in the cine storage unit 16 in advance in the ultrasound diagnostic imaging apparatus 100A. The controller 31 of the ultrasound image processing apparatus 300 sends a request for cine video data to the ultrasound diagnostic imaging apparatus 100A via the communication unit 35 in accordance with the input of the instruction to obtain the cine video data performed by an operator on the operation input unit 32. The controller 21 of the ultrasound diagnostic imaging apparatus 100A receives the above request via the communication unit 22, reads out the cine video data corresponding to the request from the cine storage unit 16, and sends the cine video data to the ultrasound image processing apparatus 300 via the communication unit 22. The controller 31 of the ultrasound image processing apparatus 300 receives the cine video data from the ultrasound diagnostic imaging apparatus 100A via the communication unit 35 and stores the cine video data in the storage unit 33.

For example, input of the instruction to execute the third cine screen information display process made by an operator via the operation input unit 32 being the trigger, the CPU of the controller 31 reads out the third cine screen information display program which is stored in the ROM, opens the program in the RAM and executes the third cine screen information generation process in cooperation with the opened program.

As shown in FIG. 10, the controller 31 executes steps S51 to S59 and ends the third cine screen information display process. Steps S51 to S59 are the process which is similar to that of steps S41 to S49 of FIG. 8. Here, the processes in the modification example corresponding to the processes performed by the cine information generating unit 15, the cine slider generating unit 18 and the display composite unit 19 in FIG. 8 are performed by the controller 31, the information in the modification example corresponding to the information stored in the cine storage unit 16 and the cine marker storage unit 17 in FIG. 8 is stored in storage unit 33, and the display 20 in FIG. 2 corresponds to the display 34 of the modification example.

By the third cine screen information display process, cine video data and cine information are stored in the storage unit 33. The controller 31 may read out the cine video data and the cine information stored in the storage unit 33 and send them to the ultrasound diagnostic imaging apparatus 100A via the communication unit 35. In such case, the controller 21 of the ultrasound diagnostic imaging apparatus 100A receives the cine video data and the cine information from the ultrasound image processing apparatus 300 via the communication unit 22 and stores them in the cine storage unit 16. Similarly to steps S38 and S39 in the second cine screen information display process of FIG. 8, the controller 21 generates cine screen information with the cine video data and the cine information stored in the storage unit 33 and displays the generated cine screen information in the display 20. In the modification example, similarly to the above described embodiment, a cine slider on which a marker indicating an operation and an operation region are arranged may also be generated.

As described above, according to the modification example, the ultrasound image processing apparatus 300 includes the controller 31 which extracts a structural object in the ultrasound image of each cine frame from the cine video data, detects an abnormal candidate spot in the extracted structural object, and generates cine information where the detected abnormal candidate spot is made to be associated with the cine frame in which the abnormal candidate spot is detected.

Thus, the position of the cine frame in which the detected abnormal candidate spot exists can be displayed by using the generated cine information. Therefore, where in the cine video data is the cine frame in which the abnormal candidate spot exists can easily be visually recognized by a reader. Further, the abnormal candidate spot in the cine video data can be detected automatically and the burden on a reader and an examiner can be reduced. Further, by the third cine screen information generation process is being executed in the ultrasound image processing apparatus 300, the amount of computation performed in the ultrasound diagnostic imaging apparatus 100A for performing ultrasound diagnosis can be reduced.

In the above description, an example where the ROM is used as a computer readable medium of a program according to the present invention is shown. However, this is not limitative in any way. As other computer readable media, a non-volatile memory such as a flash memory, a portable recording medium such as a CD-ROM, etc. can be used. Further, as a medium which provides data of programs relating to the present invention via a communication circuit, carrier wave can also be used.

The above descriptions of the embodiment and the modification example are merely examples of the preferred ultrasound image processing apparatus according to the present invention and a computer readable medium in which programs are realized, and these examples are not limitative in any way.

For example, in the above described embodiment and modification example, cine video data and cine information are separate data. However, this is not limitative in any way. Cine information may be included in cine video data (clue frame) as attached information such as tag information.

Further, in the above described embodiment and modification example, a cine screen 200 includes the ultrasound image part 210 for one ultrasound image and the cine slider part 220 is displayed as shown in FIG. 7. However, this is not limitative in any way. For example, the cine screen 200 may include thumbnails of a predetermined number of cine frames in the front and behind the cine frame shown in the ultrasound image part 210, in the order of generation, separately from the ultrasound image part 210. Further, if the cine marker and the same type range part correspond to the image data of these thumb nails, in addition to the cine slider, cine markers and the same type range part may be displayed so as to be associated with the thumb nails.

Moreover, in the above described embodiment and modification example, the ultrasound image data to be generated is B mode image data. However, this is not limitative in any way. The ultrasound image data to be generated may be volume data as three dimensional data or the like.

With respect to the ultrasound diagnostic imaging apparatus 100 and the ultrasound diagnostic imaging system 1000 in the above embodiment, detail configuration and detail operation of the components thereof may be modified as needed within the gist of the present invention.

The entire disclosure of Japanese Patent Application No. 2015-144139 filed on Jul. 21, 2015 is incorporated herein by reference in its entirety.

What is claimed is:

1. An ultrasound image processing apparatus, comprising:
   a structural object extracting unit which extracts a structural object in an ultrasound image of each frame from ultrasound image data of a plurality of continuous frames;
   an abnormal candidate spot detecting unit which detects an abnormal candidate spot in the extracted structural object;
   a cine information generating unit which generates cine information in which the detected abnormal candidate spot is made to be associated with one or more frames in which the abnormal candidate spot is detected, from among the plurality of frames of ultrasound image data; and
   a cine slider generating unit which generates, based on the cine information, a cine slider which includes a first marker indicating an abnormal candidate region corresponding to the one or more frames in which the abnormal candidate spot is detected, and a second marker indicating a frame, in the abnormal candidate region, in which the abnormal candidate spot is depicted with a maximum radius.

2. The ultrasound image processing apparatus of claim 1, wherein the cine slider is operable to receive an operation to slide and display the plurality of frames of ultrasound image data;
   wherein the first marker and the second marker include information indicating a type of the abnormal candidate spot;
   wherein the cine slider generating unit generates the cine slider such that the first marker is arranged at a position on the cine slider corresponding to the abnormal candidate region, and the second marker is arranged at a position on the cine slider corresponding to the frame in the abnormal candidate region in which the abnormal candidate spot is depicted with the maximum radius; and
   wherein the ultrasound image processing apparatus further comprises a display controller which makes the plurality of frames of ultrasound image data be displayed in a display with the generated cine slider.

3. The ultrasound image processing apparatus of claim 2, wherein, in a case where a plurality of continuous frames relating to a same type of abnormal candidate spot exist in the plurality of frames of ultrasound image data, the cine slider generating unit generates the cine slider by arranging the first marker which indicates the abnormal candidate region of the plurality of frames relating to the same type of abnormal candidate spot in the generated cine information at a position on the cine slider corresponding to the abnormal candidate region corresponding to the plurality of frames relating to the same type of the abnormal candidate spot.

4. The ultrasound image processing apparatus of claim 3, wherein the cine slider generating unit generates the cine slider by setting one frame for displaying the second marker corresponding to the type of abnormal candidate spot in the abnormal candidate region relating to the same type of abnormal candidate spot, and by arranging the second marker at a position of the set frame on the cine sider.

5. The ultrasound image processing apparatus of claim 3, wherein the cine slider generating unit generates the cine slider by setting different colors according to types of abnormal candidate spot to display the first marker indicating the abnormal candidate region and/or the second marker relating to the same type of abnormal candidate spot as the first marker.

6. The ultrasound image processing apparatus of claim 1, wherein the cine information generating unit generates the cine information including operating information where a type of operation performed when generating the plurality of frames of ultrasound image data is made to be associated with a frame which is subject to the operation.

7. The ultrasound image processing apparatus of claim 2, wherein:
   the cine information generating unit generates the cine information including operating information where a type of operation performed when generating the plurality of frames of ultrasound image data is made to be associated with a frame which is subject to the operation, and
   the cine slider generating unit generates the cine slider by arranging a third marker corresponding to the type of operation in the generated cine information at a position of a frame which is subject to the operation.

8. The ultrasound image processing apparatus of claim 1, further comprising:
   a transmitting unit which transmits a driving signal to an ultrasound prove which transmits and receives ultrasound waves to and from a subject;
   a receiving unit which receives a received signal from the ultrasound probe; and
   an image generating unit which sequentially generates the plurality of frames of image data from the received signal.

9. The ultrasound image processing apparatus of claim 1, wherein the abnormal candidate spot detecting unit detects a tumor as the abnormal candidate spot, and wherein the second marker indicates the frame, in the abnormal candidate region, in which the tumor is depicted with a maximum radius.

10. A computer readable non-transitory medium which realizes a program to make a computer function as:
a structural object extraction unit which extracts a structural object in an ultrasound image of each frame from ultrasound image data of a plurality of continuous frames;
an abnormal candidate spot detecting unit which detects an abnormal candidate spot in the extracted structural object;
a cine information generating unit which generates cine information in which the detected abnormal candidate spot is made to be associated with one or more frames in which the abnormal candidate spot is detected, from among the plurality of frames of ultrasound image data; and
a cine slider generating unit which generates, based on the cine information, a cine slider which includes a first marker indicating an abnormal candidate region corresponding to the one or more frames in which the abnormal candidate spot is detected, and a second marker indicating a frame, in the abnormal candidate region, in which the abnormal candidate spot is depicted with a maximum radius.

11. The computer readable non-transitory medium of claim 10,
wherein the abnormal candidate spot detecting unit detects a tumor as the abnormal candidate spot, and
wherein the second marker indicates the frame, in the abnormal candidate region, in which the tumor is depicted with a maximum radius.

12. An ultrasound image processing apparatus, comprising:
a display which is configured to display a plurality of continuous frames of ultrasound image data; and
a hardware circuit which is configured to:
extract a structural object in an ultrasound image of each frame from ultrasound image data of the plurality of continuous frames,
detect an abnormal candidate spot in the extracted structural object,
generate cine information in which the detected abnormal candidate spot is made to be associated with one or more frames in which the abnormal candidate spot is detected, from among the plurality of frames of ultrasound image data; and
generate, based on the cine information, a cine slider which includes a first marker indicating an abnormal candidate region corresponding to the one or more frames in which the abnormal candidate spot is detected, and a second marker indicating a frame, in the abnormal candidate region, in which the abnormal candidate spot is depicted with a maximum radius.

13. The ultrasound image processing apparatus of claim 12,
wherein the hardware circuit detects a tumor as the abnormal candidate spot, and
wherein the second marker indicates the frame, in the abnormal candidate region, in which the tumor is depicted with a maximum radius.

* * * * *